United States Patent [19]

Behl

[11] Patent Number: 5,275,611
[45] Date of Patent: Jan. 4, 1994

[54] TENSION GUIDE AND DILATOR

[75] Inventor: Robert S. Behl, Palo Alto, Calif.

[73] Assignee: InnerDyne Medical, Inc., Mountain View, Calif.

[21] Appl. No.: 913,129

[22] Filed: Jul. 13, 1992

Related U.S. Application Data

[62] Division of Ser. No. 616,122, Nov. 20, 1990, abandoned.

[51] Int. Cl.$^5$ .............................................. A61M 29/00
[52] U.S. Cl. .................................. 606/198; 604/164; 604/264; 604/280; 128/772
[58] Field of Search ............................ 604/158-; 606/198, 192, 194; 128/657, 772

[56] References Cited

U.S. PATENT DOCUMENTS

| | | |
|---|---|---|
| 1,213,001 | 1/1917 | Philips . |
| 1,248,492 | 12/1917 | Hill . |
| 3,545,443 | 12/1970 | Ansari . |
| 3,742,958 | 7/1973 | Rundles . |
| 4,043,346 | 8/1977 | Mobley et al. ............... 604/106 |
| 4,502,482 | 3/1985 | DeLuccia et al. ............ 604/166 |
| 4,581,025 | 4/1986 | Timmermans . |
| 4,649,916 | 3/1987 | Frimberger ................... 604/164 |
| 4,654,028 | 3/1987 | Suma ............................. 604/106 |
| 4,737,141 | 4/1988 | Spits ............................... 604/28 |
| 4,757,827 | 7/1988 | Buchbinder et al. . |
| 4,772,266 | 9/1988 | Groshong . |
| 4,798,593 | 1/1989 | Iwatschenko ................. 128/657 |
| 4,844,092 | 7/1989 | Rydell et al. .................. 604/164 |
| 4,865,593 | 9/1989 | Ogawa et al. . |
| 4,888,000 | 12/1989 | McQuilkin et al. . |
| 4,932,959 | 7/1990 | Horzewski ..................... 604/165 |
| 4,994,027 | 2/1991 | Farrell ............................. 604/53 |
| 5,002,558 | 3/1991 | Klein et al. ..................... 600/192 |
| 5,024,658 | 6/1991 | Kozlov et al. ................... 604/96 |

FOREIGN PATENT DOCUMENTS 627828 10/1978 U.S.S.R. .

OTHER PUBLICATIONS

Full Core TM Biopsy Gun brochure, Amedic AB, Sweden, 6 pp.
Huibregtse, "Endoscopic Biliary and Pancreatic Drainage," pp. 3-5 (1 Technique and materials).
National-Standard Medical Products, Gainesville, Florida "Hawkins TM Breast Localization Needle".

*Primary Examiner*—C. Fred Rosenbaum
*Assistant Examiner*—Chalin Smith
*Attorney, Agent, or Firm*—Townsend and Townsend Khourie and Crew

[57] ABSTRACT

A dilator assembly for forming and enlarging percutaneous penetrations into body cavities includes an elongate guide member and one or more elongate dilation members. The guide member includes a retractable anchor near its distal end so that an outward force or tension may be maintained on the body cavity wall as successfully larger dilators are introduced over the guide member. In this way, the alignment of the guide member is maintained along the initial penetration and the tendency for the wall of the body cavity to separate from and invaginate into the surrounding fascia is reduced. Alternatively, means may be provided for internally tensioning or stiffening the guide member so that the guide member will remain aligned and resist withdrawal, buckling, and kinking as a dilator or working catheter is introduced.

19 Claims, 6 Drawing Sheets

TENSION GUIDE AND DILATOR

This is a division of application Ser. No. 07/616,122, filed Nov. 20, 1990, now abandoned.

BACKGROUND OF THE INVENTION

1. Field of the Invention

The present invention relates generally to apparatus and methods for providing percutaneous access into the interior of body cavities. More particularly, the present invention relates to the construction and use of an apparatus for introducing one or more dilating members to provide a relatively large penetration to the hollow body cavity.

The need to percutaneously penetrate a patient's skin in order to provide access into the interior of a hollow body organ arises under a variety of circumstances. For example, various catheters, cannulas, and the like, may be introduced in order to aspirate the body cavity, introduce medication into the body cavity, perform an interventional procedure within the body cavity, and the like. Numerous devices and methods have been developed in order to provide suitable penetrations for different procedures.

One common approach for providing access to the interior of a body cavity utilizes a trocar and cannula assembly. The trocar is a metal rod with a sharp tip, while the cannula is a hollow tube which receives the trocar in its axial lumen. With the trocar in place so that its sharpened tip extends forward of the cannula, the assembly can be introduced into the body cavity, typically through a small puncture hole. The trocar is then removed, and the cannula remains in place with its lumen providing access to the interior of the body cavity.

Such trocar and cannula assemblies have been used for many years and continue to be adequate for many conventional procedures. A major limitation exists, however, when it is desired to introduce a relatively large catheter or other device through the puncture hole surrounding the cannula. The initial puncture hole is typically small and must be dilated so that larger devices can be introduced. Dilation is typically accomplished by successively introducing one or more dilating rods having increasingly large diameters through the puncture hole and into the hollow organ, typically over a flexible guide wire which has been introduced through the cannula, with the cannula then being removed. Dilating rods typically have a tapered distal end in order to facilitate their introduction and a small central lumen to receive the guide wire. The use of such conventional dilating rods is generally successful when entering cavities which are relatively close to the skin and/or which are restrained from axial movement by their structure or by attachment to surrounding fascia.

The use of dilating rods is less successful with body organs which are not axially constrained, such as the gall bladder, urinary bladder, stomach, and the like, and which have a tendency to move away from and resist entry of even a highly tapered dilating rod. This problem is worsened by the tendency of the flexible guide wire to buckle or bow slightly at the point of entry and for the unconstrained distal of the guide wire to be pulled out of position within the hollow body organ. The resulting misalignment of the guide wire and the entry path formed by the guide wire can exacerbate the problem of dilating the puncture access by causing bowing and invagination of the structure wall and tearing of the body organ away from the surrounding fascia.

Various techniques and devices have been developed to at least partly overcome these problems. For example, dilators having very small incremental increases in diameter combined with very gradually tapered distal ends can reduce the incidence of fascial detachment. That approach, however, is not always successful and the need to employ longer, more tapered dilators and/or a greater number of dilators greatly increases difficulty of manipulating the dilators and/or the time necessary for performing the procedure.

An alternate approach to prevent fascial detachment of the internal body organ has been the use of multiple separate anchors or toggles which are placed peripherally about the site of the primary puncture in order to more strongly attach the body organ to its surrounding fascia. Such an approach is generally workable, but requires a separate puncture for each anchor and subsequent suturing of each anchor in place. Again, such an approach increases patient discomfort as well as the time necessary to perform the procedure.

For these reasons, it would be desirable to provide improved methods and apparatus for forming and enlarging percutaneous penetrations into hollow body organs and cavities. The apparatus and methods should minimize additional time and complexity required for performing any associated interventional procedure, and in particular should avoid the need to make secondary penetrations in order to help secure the body organ to the surrounding fascia. The methods should be suitable for introducing dilators of virtually any diameter, including very large diameters on the order of 20 French, 24 French, and larger while avoiding buckling and misalignment of the dilator guide member. Moreover, the methods and apparatus should be compatible with virtually any type of interventional procedure which requires the formation of a percutaneous penetration for access to the interior of a body cavity.

2. Description of the Background Art

U.S. Pat. No. 4,772,266, describes a dilator/sheath assembly that may be passed over an in-dwelling guide wire in order to enlarge an access hole, with entry of the sheath further enlarging the hole. U.S. Pat. No. 1,213,001, describes a trocar and cannula assembly which includes an intermediate tube to form a three-piece structure. U.S. Pat. No. 3,742,958, discloses a cannula having an axial slot to allow the cannula to be stripped from a working catheter which has been introduced through the cannula. U.S. Pat. Nos. 4,888,000; 4,865,593; 4,581,025; 3,545,443; and 1,248,492, each describe devices suitable for percutaneous penetration of a body cavity, blood vessel, or solid tissue. The disclosures of each of the U.S. Patents cited in this paragraph are hereby incorporated herein by reference. Huibregtse, *Endoscopic Biliary and Pancreatic Drainage*, pages 3–5, (1988) describes the use of a Fogarty balloon catheter to introduce an endoprosthesis through a bile duct stenosis. National-Standard Medical Products, Gainesville, Fla., sells a marking needle with a retractable barb for insertion near a tumor mass, as described in a product description sheet entitled "Hawkins TM Breast Localization Needle."

Methods which rely on the percutaneous introduction of a catheter into the gall bladder and other hollow body organs are described in copending application Ser.

Nos. 07/407,839; 07/529,077; and 07/551,971, the disclosures of which are incorporated herein by reference.

SUMMARY OF THE INVENTION

According to the present invention, improved apparatus and procedures for forming and enlarging percutaneous penetrations into hollow body organs and cavities are provided. The apparatus comprises an elongate guide member having proximal and distal ends and means for maintaining the guide member under tension during the enlargement phase of the procedure. Conveniently, the tension means may be a means for anchoring the guide member within the body cavity. Alternatively, the tension means may be a means for controlling the stiffness of the guide means along all or part of its length. The apparatus further comprises one or more elongate dilation members which may be introduced to the body cavity over a path defined by the guide member. Tension on the guide member is advantageous in at least two respects. First, such tension causes the anchor means to pull outwardly against the inner surface of the body cavity proximate the penetration, reducing the tendency for the organ wall to deform or detach from surrounding fascia as the dilation member(s) are introduced. Second, the tension minimizes the tendency for flexible guide members to buckle or become misaligned as the dilation members are introduced. Such buckling and misalignment can cause the dilation members to deviate from the desired penetration path.

The specific structure of the guide member and the dilator(s) will vary depending on the nature of the organ which is to be accessed. The guide member and/or dilators may be substantially rigid or substantially flexible, depending on the tortuosity of the entry route to the body cavity. For relatively accessible organs which can be approached over a generally straight path, the guide member will usually be rigid and be introduced by means of an integrally sharpened end or an interior stylet in a manner similar to the introduction of a cannula using a trocar. For less accessible organs which require a tortuous approach path, the guide member will usually be flexible in the manner of a flexible guide wire. In either case, the anchor means on the guide member will usually be retractable or collapsible so that the guide member can be inserted (or removed) with the anchor retracted, and the anchor extended only after the distal end of the guide member has reached the interior of the body cavity. A suitable stiffening means may be an internal stiffening wire which is selectively introduced to the guide member to exert tension over the length of the member by application of force on the distal end of the member. The dilator(s) will usually be introduced directly over the guide member, typically using a passage or slot formed axially in the dilator to receive the exterior of the guide member. Alternatively, a separate rail, track, guide wire, or the like, may be attached to the guide member and the dilators introduced over said separate element.

In a first specific embodiment, the guide member is tubular having a central lumen. The anchoring means is a deflectable element which is secured near the distal end of the tubular guide member and which is able to assume a retracted configuration within the lumen or an extended configuration where it projects radially across the lumen and out an aperture formed in the opposite wall of the cylindrical guide member. Usually, the deflectable element is spring-mounted so that it assumes the radially-projecting configuration when unconstrained. In the latter case, a stylet will be slidably disposed within the lumen so that it can move (and maintain) the deflectable element into its retracted configuration. Thus, the assembly of the tubular guide member and stylet can be first introduced in the body cavity, typically with the stylet having a sharpened end to facilitate entry. Once the anchor member is in place, the stylet is removed so that the deflectable element assumes its extended configuration. The guide member can then be pulled outwards or backwards so that the deflectable element is urged against the inner surface of the body cavity and tension maintained on the guide member. While maintaining such tension, a dilator having an axial slot can be introduced over the guide member. The axial slot slidably receives the guide member and is aligned to accommodate the deflectable element as the dilator reaches the distal end of the guide member. The dilator can be removed and replaced by successively larger dilators in a similar manner until a penetration having a desired diameter is formed. Tension will be maintained on the guide member during the entire procedure so that pressure applied by the deflectable element will inhibit detachment of the proximal wall of the body organ or cavity from the surrounding fascia. Such tension further maintains alignment of the guide member through the initial path of the puncture through the successive layers of tissue and resists buckling of the guide member caused by the applied compressive force of the dilator(s). In this way, the enlarged penetration will be formed along the desired path defined by the initial placement of the guide member.

In an alternate embodiment, the elongate guide member may be a flexible hollow member, such as a flexible catheter or flexible guidewire. The flexible elongate member may be introduced to a desired hollow body organ, either through a penetration, through internal ducts and passages which naturally connect to the hollow body organ, or through a combination thereof. After the flexible elongate member is in place, an internal stiffening member, such as a solid core wire, is introduced through a central lumen of the flexible elongate member so that the distal end of the stiffening member engages the distal end of the flexible elongate member. The stiffening member may then be used to apply tension on to the distal end of the flexible elongate member, thus stiffening the resulting assembly which includes both the flexible elongate member and the internal stiffening member. The stiffened elongate member assembly may then be used in order to introduce a larger dilator and/or working catheter over its exterior in a conventional manner. In this way, a guiding path is defined by the assembly which is much stiffer than that which could be introduced initially, particularly if passing through a tortuous path. The stiffened assembly may provide additional benefits in certain anatomies. For tortuous paths, the stiffened member will tend to straighten the path, frequently reducing the curvature and facilitating the introduction of the catheter/dilator. The stiffened assembly may also tend to imbed or lock itself in place within a restricted passage further anchoring the member in place as a catheter/dilator is introduced thereover.

In an exemplary method according to the present invention, the flexible guide member assembly just described is introduced to the gall bladder through the duodenum, common bile duct, and cystic duct.

DESCRIPTION OF THE PREFERRED EMBODIMENT

The present invention is useful for forming and dilating percutaneous penetrations into a variety of hollow organ bodies and cavities for a multiplicity of purposes. The sizes of the initial penetrations and subsequent dilations are not critical and may vary widely. The initial penetration will usually be a very small puncture formed using a needle or other small instrument in order to minimize trauma to the patient. Depending on the target organ, the puncture instrument may have a size in the range from about 3 French (F) (where one French equals 0.33 millimeters) to about 8 F, and usually being in the range from about 4 F to 6 F. The initial penetration will typically be dilated to a final diameter from about 10 F to about 30 F, typically being from about 12 F to 28 F and usually being from about 14 F to 24 F, with the present invention being particularly useful for the formation of larger diameter penetrations. The purpose of the penetration can be for drainage, intraorgan drug administration, feeding, perfusion, aspiration, or the like, but will usually be for the introduction of a relatively large working catheter, such as those intended for interventional procedures. Such interventional procedures include laparoscopy, balloon dilatation of ducts, placement of stents, and the like. Penetrations are particularly suitable for the placement of gastrointestinal feeding tubes as well as for the introduction of thermal ablation catheters, such as those described in copending applications Ser. Nos. 07/407,829; 07/529,077; and 07/551,971, previously incorporated herein by reference.

The percutaneous penetrations may be formed into virtually any hollow body organ or cavity, particularly including the gall bladder, stomach, urinary bladder, uterus, kidney, portions of the lung, and the like. The methods and apparatus of the present invention are also useful for providing penetrations into blood vessels and other small hollow body structures and ducts. The latter penetrations will often require a flexible guide member to gain access while the former penetrations can frequently be achieved with a relatively rigid guide member.

A dilation assembly according to the present invention includes an elongate guide member which defines a path for the introduction of one or more dilation members into the body cavity. The guide member will have proximal and distal ends, and may have a generally flexible or rigid structure, depending on the particular application. Rigid guide members will generally be employed when the target organ may be approached along a substantially straight path, while flexible guide members will normally be used when a tortuous path must be followed. Rigid guide members may be formed from metals, typically stainless steel, rigid plastics, and the like, while flexible guide members will typically be formed from coiled stainless steel or Nitinol ™ wire or from extruded organic polymers, such as silicone rubber, polyurethane, polyvinylchloride, nylon, and the like. In the latter case, reinforcement may be provided in order to provide a particular degree of flexibility suitable for the intended application.

The length of the guide member will vary, with shorter guide members having length in the range from about 10 to 20 cm being suitable for accessing body cavities which are near the surface of the skin, such as the stomach. Longer guide members having a length in the range from about 20 to 40 cm will be suitable for body cavities, such as the kidney. Even longer flexible members in the nature of a guide wire may be employed for inserting dilating members to blood vessels and other remote ducts. In such cases, the length of the guide wire may be in the range from about 40 cm to 150 cm, or longer.

Generally, the shorter guide members which are used for accessing less remote body organs along a straight path will have a generally rigid structure, while longer guide members intended for accessing more remote body organs and ducts along a tortuous path will have a flexible structure. This correlation, however, will not always be the case, and it may frequently be desirable to utilize a flexible guide member to access hollow body organs along short, straight access paths.

The guide member may have a solid cross-section, i.e. in the form of a solid rod or wire, but more usually will be tubular having a central or axial lumen therethrough. The axial lumen allows the guide member to be introduced using a stylet (as described in more detail hereinbelow) or in the case of flexible guide members, to be introduced over a movable guide wire in a conventional manner. In some cases, of course, the guide member itself may be in the nature of a guide wire, e.g., being formed from nested coils in a known manner.

Means for maintaining the guide member under tension will be provided in combination with the guide member. Usually, the tension means will comprise an anchor means located near the distal end of the guide member, whereby the distal end may be secured within the hollow body organ or other remote location and tension may be applied by pulling outwardly on the proximal end of the guide member which remains external to the patient. Other tension means, however, may also find use. For example, a separate elongate stiffening member may be inserted coaxially within or outside of the guide member in order to provide a desired tension thereon. Alternatively, the tension means may comprise means for internally pressurizing the guide member in order to provide the desired elongating tension. Other approaches for tensioning the guide member will be obvious to those skilled in the art in view of the teachings herein.

Means for anchoring the guide member within the hollow body organ will provided at or near the distal end of the guide member. The anchoring means will be typically retractable or collapsible so that the guide member can be introduced and withdrawn without interference from the anchor. The anchor means is selectively extended or expanded outward from the guide member so that it can engage a structure within the hollow body organ or a nearby region. Tension is then applied by pulling or drawing outwardly on the guide member. In a situation where the guide member penetrates a body cavity, the anchor will usually engage a region of the inner surface of the body cavity proximate the penetration. By thus maintaining a constant tension on the anchoring means, the wall of the body cavity can be held in place and prevented from detaching from the proximal and surrounding fascia during subsequent dilation procedures.

The structure of the anchoring means is not critical. For example, the anchoring means may be an inflatable balloon which, when in place within a restricted region of the body organ or adjacent duct, may be inflated to become lodged therein. Alternatively, the anchor may be a portion of a flexible guide member, where the portion may be stiffened so that it will become lodged within a tortuous region of a duct or hollow organ to prevent withdrawal of the guide member. Conveniently, the anchor can be a deflectable element which is actuated mechanically, such as using a cable or other actuation means within the guide member. Alternatively, the deflectable element can be formed from a shape memory alloy which is released from a restraining structure or selectively actuated by a heater which is externally powered.

In an exemplary embodiment, the anchoring means is a spring-mounted deflectable finger which is mounted on the inner wall of a tubular or cylindrical guide member. When unconstrained, the finger extends laterally through an aperture in the opposing wall so that it may engage the inner surface of the body organ. Numerous alternative mechanical, electromechanical, and other systems for providing a deflectable element or other anchor means will be apparent to those skilled in the art.

The system of the present invention will include one or more dilation members which include a means for following the path defined by the guide member when it extends percutaneously into the hollow body organ. In a preferred embodiment, the system will include a plurality of dilation members which are generally similar in construction, but which have successively larger cross-sectional areas so that the size of the percutaneous penetration can be increased by introducing successively larger dilators over the guide member. Usually, the path following means will be an axial channel formed on one side of the dilator so that it can be passed over the guide member while allowing clearance for the deflectable element. When the dilation member includes an axial channel, it will be desirable to provide keying means near the proximal end of the guide member so that the slot on the axial channel may be radially aligned with the anchor means on the distal end of the guide member. In this way, the slot will necessarily be able to pass the anchoring means, e.g., a radially extending deflectable element, when the dilator reaches the anchoring means. Usually, the dilator will be tapered at its distal end to facilitate penetration, and the dilator may optionally include one or more additional lumens for other purposes, such as the introduction of a separate movable guide wire which can remain in place after the dilator and guide member are removed from the enlarged penetration. The dilation members will typically have circular cross-sections, although other cross-sectional shapes might also find use.

The size of the dilation members will typically vary from relatively small, i.e. as low as about 10 F, to relatively large, i.e., as large as about 30 F. The incremental increase in size between successfully larger dilators will typically be on the order of about 3 F to 6 F, more usually being about 4 F to 5 F. Thus, it may be necessary to employ as many as about five dilators to form a relatively large penetration on the order of about 30 F. Of course, the permissible incremental increase in the dilator size will depend greatly on the elasticity of the tissue being dilated, the fragility of the attachment of the body organ to the surrounding fascia, and the bearing surface area of the anchor being utilized. Where the tissue elasticity is lower, fascia attachment more fragile, and/or the bearing surface area reduced, the incremental increase in dilator diameter should be smaller.

Figure 5:
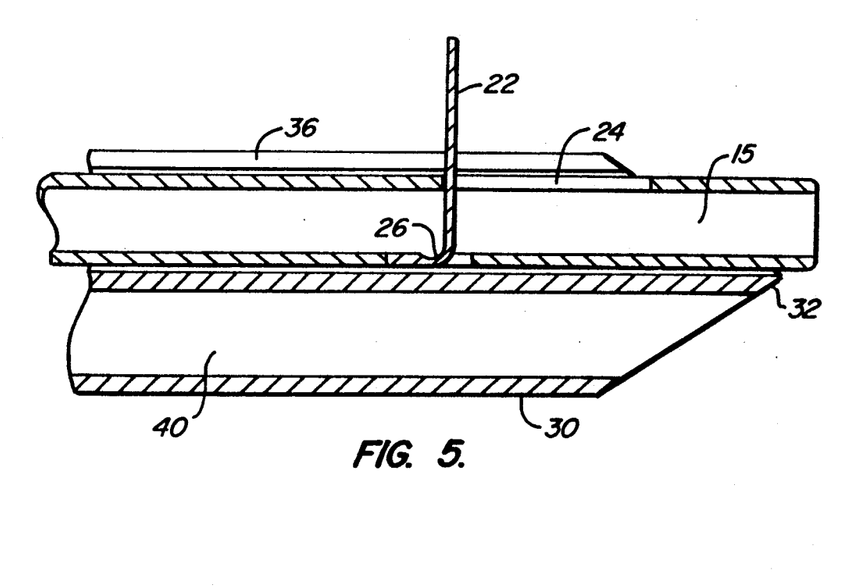
FIG. 5 is a cross-sectional view taken along line 5—5 of FIG. 4.

Referring now to FIGS. 1–5, a dilator assembly 10 constructed in accordance with the principles of the present invention includes a stylet 11 having a sharpened distal end 12 and a handle 14 at its proximal end. The stylet 11 is received in an axial lumen 15 of a tubular guide member 16 having a proximal end 18 and distal end 20. A deflectable element 22 is disposed in the lumen 15 having its length generally aligned with the axis of the lumen (when the stylet 11 is in position). An aperture 24 is formed in the wall of the tubular guide member 16 at a location generally opposite to that from the deflectable element 22. The deflectable element is a spring which in its unconstrained configuration (i.e., with the stylet 11 removed from axial lumen 15), assumes the radially extended position illustrated in broken line in FIG. 2 and in solid line in FIG. 5. With the stylet in place, however, the deflectable element 22 is deflected downward in a retracted position, as illustrated in full line in FIG. 2. In this way, the deflectable element 22 is in its retracted configuration when the assembly of the guide member 16 and stylet 11 is introduced to or withdrawn from the body cavity, as described in more detail hereinafter. The deflectable element 22 may be released into its extended configuration by simply withdrawing the stylet 11 which allows the deflectable element to assume its unconstrained configuration, as illustrated in FIG. 5.

The third component of the dilator assembly 10 is a dilator 30 which is a generally cylindrical tube having a tapered distal end 32 and an axial slot 36. The axial lumen 34 is sized so that it may pass over the exterior of guide member 16, while the slot 34 will be sufficiently large to snap over the guide member. The opening of slot 36 provides clearance so that the dilator 30 may be advanced past the deflectable element 22 when the dilator 30 is introduced into the body cavity, as described hereinafter. Such clearance is best observed in FIG. 4. Keying means, such as tab 37 formed on the distal end of guide member 16 (FIGS. 1 and 2), assures that the slot 36 will be properly aligned with the deflectable element 22 as the dilator 30 is advanced forwardly down the guide member. A lumen 40 is optionally provided in the dilator 30, and can be used for introducing a guide wire into the percutaneous penetration after the dilation procedure has been completed. Once passing the guide wire in through the lumen 40, the entire dilator assembly including the dilator 30, guide member 16, and stylet 11 may be removed leaving the guide wire in place.

While only one dilator 30 is illustrated, it will be appreciated that a plurality of dilators having successively larger diameters may be provided in order to practice the method of the present invention, as described in more detail hereinafter. A particular advantage of the present invention derives from the maintenance of tension on the guide member which results in a compressive force on the tissues which are being penetrated. Such a compressive force tends to hold various layers of the tissue together as the dilator(s) are introduced, allowing the use of larger diameter dilators than would otherwise be possible without tearing or separating tissue layers. Thus, the total number of dilators required to achieve the penetration of a given size may be reduced.

Figure 6:
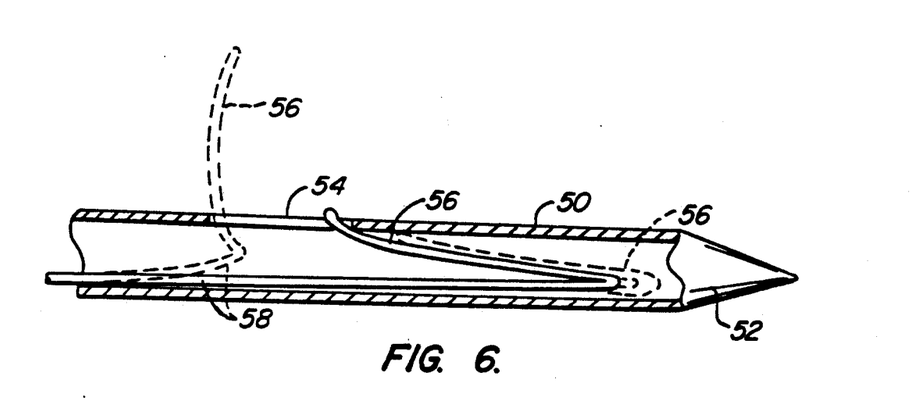
FIG. 6 is an alternate embodiment of the guide member which can be used with the dilator of FIGS. 1-5.

Referring now to FIGS. 6-9, construction of several alternative anchoring means will be described. In FIG. 6, a guide member 50 comprises a hollow needle having a sharpened distal tip 52. An aperture 54 in the side of the guide member 50 allows a spring tip 56 of an anchor wire 58 to project outwardly, as illustrated in broken line. Initially, the spring tip 56 is fully doubled-back (as shown in the right hand broken line position), and the spring tip moves out through the aperture as the anchor wire is drawn proximally (to the left in FIG. 6). In this way, the guide member 50 may be introduced through a pre-formed incision and dilator(s) similar to those illustrated in FIGS. 1-5, introduced thereover after the spring tip 56 has been released.

Figure 1:
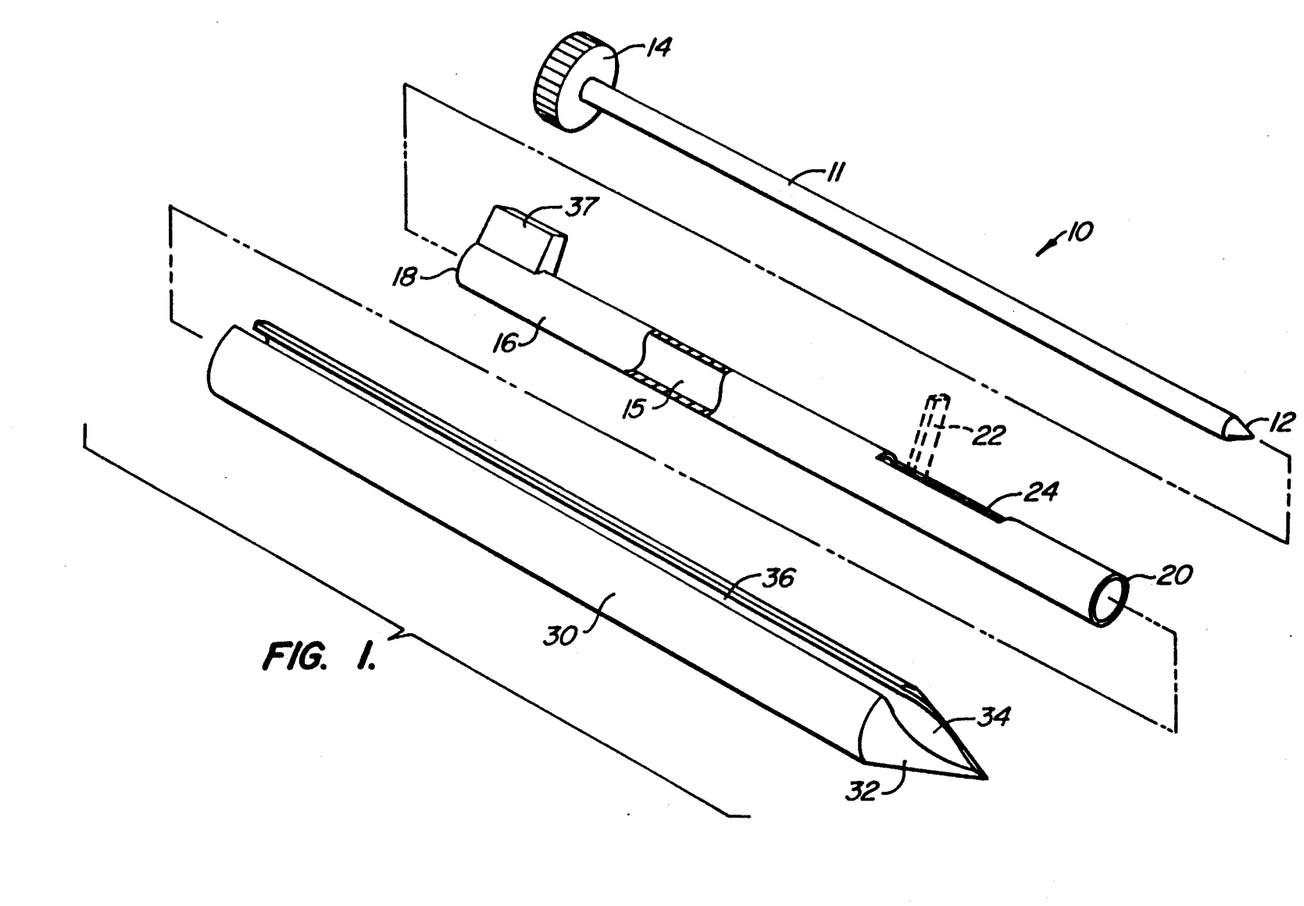
FIG. 1 illustrates a specific dilator assembly constructed in accordance with the principles of the present invention.
Figure 2:
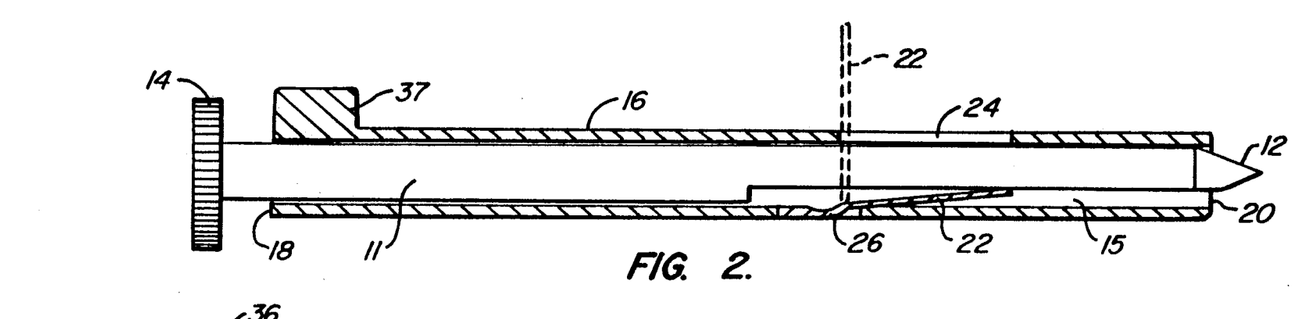
FIG. 2 is an elevational view of the guide member and stylet of the dilator assembly of FIG. 1, shown with the guide member in section.
Figures 3, 4:
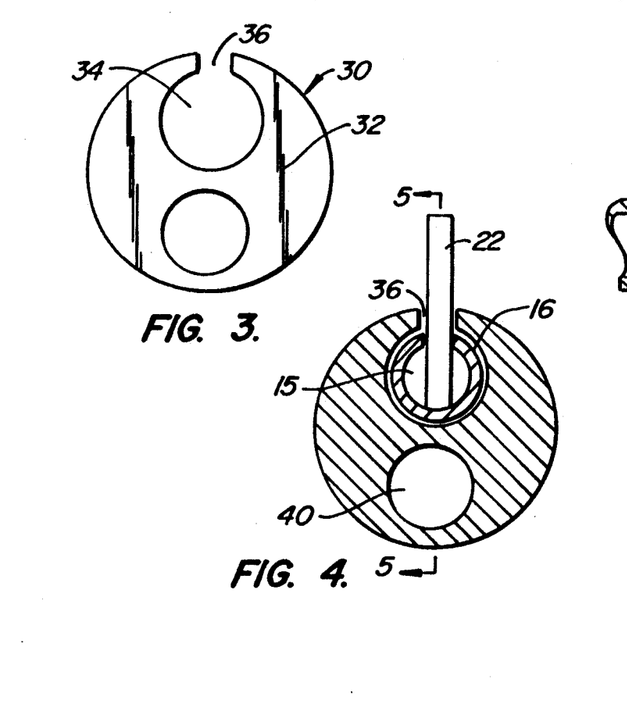
FIG. 3 is a front end view of the dilator element of the dilator assembly of FIG. 1.
FIG. 4 is a cross-sectional view of the dilator element shown with the guide member in place.

The guide member of FIG. 6 can be modified to permit introduction using a removable stylet, similar to stylet 11 in FIGS. 1 and 2. In such a modification (not illustrated), sharpened tip 52 would be removed from the shaft, and the distal tip left open. The guide member 50 would then be introduced with the stylet providing the sharpened tip. After placement of the guide member, the stylet would be removed and the anchor wire 58 will be inserted into the lumen of the guide wire. Optionally, the anchor wire could be contained in a loading tube which maintains the wire in its folded configuration as it is inserted into the guide member.

Figure 7:
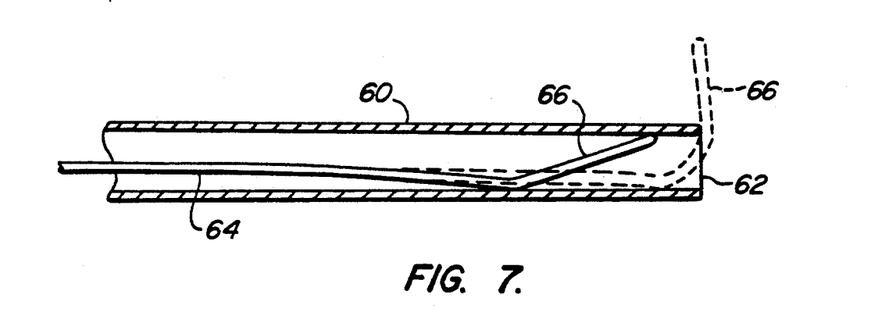
FIG. 7 is a second alternate embodiment of the guide member of the present invention that can be used with the dilator of FIGS. 1-5.

A second alternative anchoring means is illustrated in FIG. 7, where a guide member 60 having an open distal end 62 receives an anchor wire 64 which has an "L" shaped tip when unconstrained. The guide member 60 may be introduced to a hollow body cavity over a separate guide wire, removable hub, or needle in a conventional manner. Conversely, the guide member 60 may be introduced with a sharpened stylet which is subsequently removed. After optionally removing the stylet, guide wire or needle, the anchor wire 64 may be inserted so that a forward spring tip 66 is released from the open distal end 62 and assumes the deflected configuration shown in broken line. Conveniently, the anchor wires 58 (FIG. 6) and 64 (FIG. 7) may be formed from a conventional spring stainless steel or from a high memory alloy, such as Nitinol TM. A loader tube which constrains the spring in an appropriate attitude could be used to simplify loading.

Figure 8:
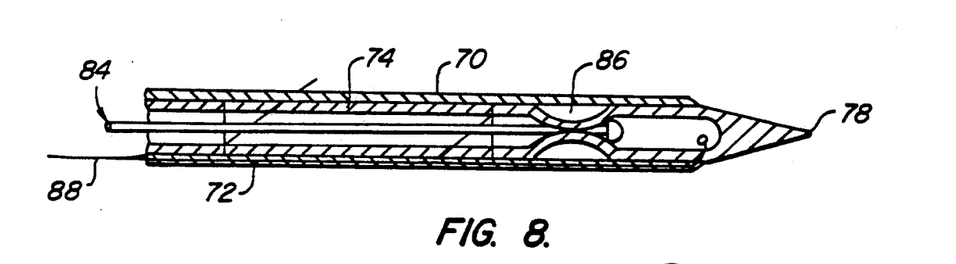
FIGS. 8 and 9 illustrate a third alternate embodiment of the guide member of the present invention that can be used with the dilator of FIGS. 1-5.
Figure 9:
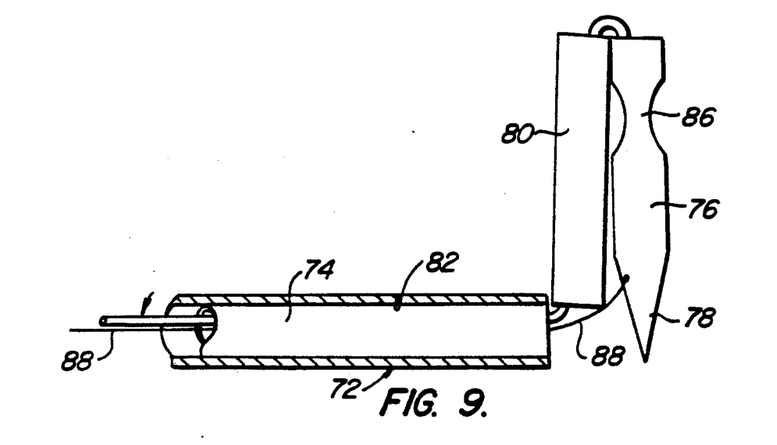

Referring now to FIGS. 8 and 9, a third alternate embodiment for a guide member 70 is illustrated. Guide member 70 includes an outer rigid cannula 72 and an inner segmented rod 74. Rod 74 includes a distal segment 76 having a sharpened distal tip 78, an intermediate segment 80, and a proximal segment 82. The segments 76, 80, and 82, are generally hollow and held together by an elastic member 84 which is secured within the distal segment 76 by a swaged region 86 formed in the distal segment. After the guide member is in place with its distal end within the desired region of the hollow body cavity, the outer cannula 72 may be withdrawn in the proximal direction so that the distal segment 76 and intermediate segment 80 of the inner rod 74 are exposed. In order to collapse the distal structure of the rod 74, tension may be applied to a suture 88 which is secured to the tip of distal segment 76 of the rod member 74. In this way, the distal segment 76 and intermediate segment 80 may be collapsed to the configuration illustrated in FIG. 9. Dilating members (not illustrated) may then be advanced over the outer cannula 70 with the collapsed segments 76 and 80 of the inner rod serving as the anchor means.

Figure 10:
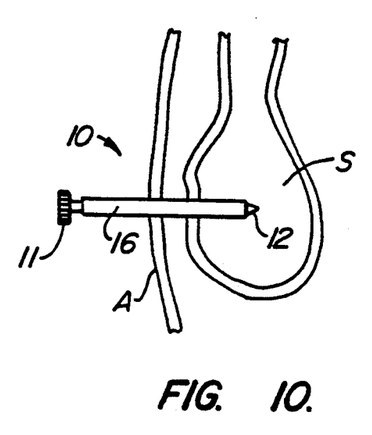
FIGS. 10-12 illustrate a method performed in accordance with the principles of the present invention utilizing the dilator assembly of FIGS. 1-5.
Figure 11:
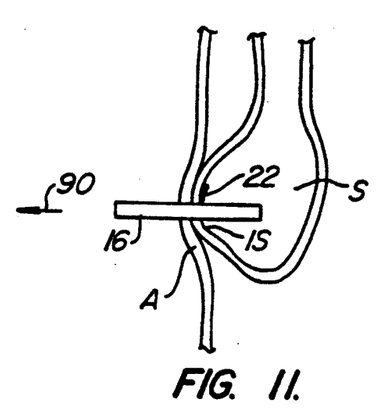
Figure 12:
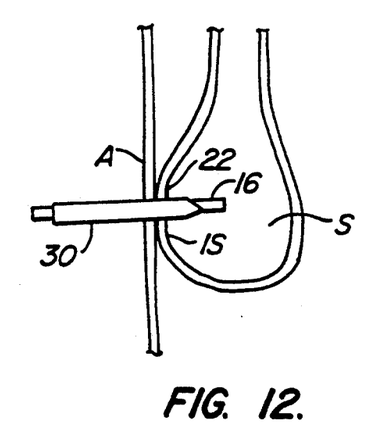

Referring now to FIGS. 10-12, use of the dilator assembly 10 of FIGS. 1-5 for forming a percutaneous penetration through the abdomen A into a stomach S is illustrated. Initially, the assembly 10 including the guide member 16 and stylet 11 is introduced through the abdominal wall A using the sharp protruding end 12 of the stylet to provide access. Optionally, an initial penetration could be made using a needle or other penetrating device. After the guide member 16 has been introduced, the stylet 11 is removed, allowing the deflectable element 22 to assume its extended configuration from guide member 16, as illustrated in FIG. 11. The guide member 16 is then pulled outwardly in the direction of arrow 90 so that the deflectable element 22 engages the inner surface IS of the stomach in the region of the penetration. As illustrated in FIG. 7, placing the guide member 16 under tension pulls the inner wall of the stomach S against the overlying fascia. A first dilation member 30 may then be introduced over the guide member 16 while maintaining tension on the guide member 16, as illustrated in FIG. 8. The number and size of dilators 30 which are finally used will depend on the desired size of the percutaneous penetration. After the desired size is achieved, the tension is released by moving guide member 16 forward to disengage element 22 from the inner surface IS of stomach S. A guide wire may optionally be introduced through a second lumen 40 (FIGS. 2-5) that may be incorporated into the larger dilators. The stylet 11 will be reintroduced to the guide member 16 so that the deflectable element 22 is retracted. The dilator 30, guide member 16, and stylet 11 may then be withdrawn from the penetration, leaving the guide wire in place within a relatively large tract suitable for insertion of a large sheath or working catheter.

Figure 13:
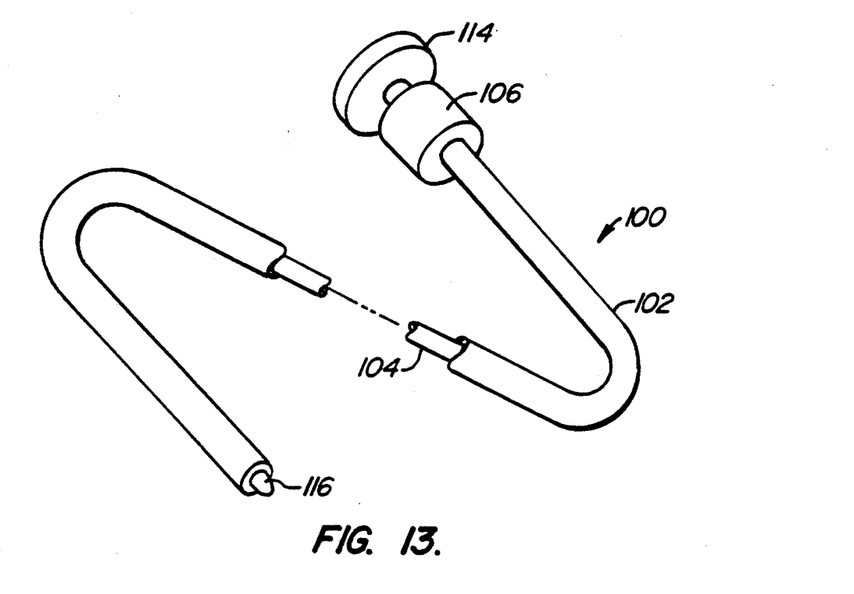
FIG. 13 illustrates an apparatus constructed in accordance with the principles of the present invention useful for introducing dilators and/or working catheters to hollow body organs through tortuous paths.
Figure 14:
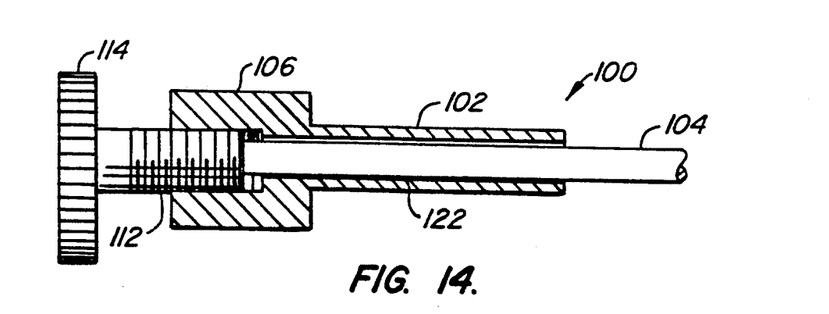
FIG. 14 is a detailed view of the proximal end of the apparatus of FIG. 13, shown in cross-section.
Figure 15:
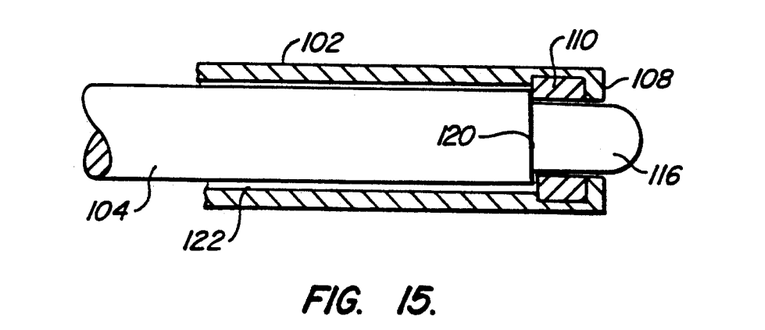
FIG. 15 is a detailed view of the distal end of the apparatus of FIG. 13, shown in cross-section.

Referring to FIGS. 13-15, an elongate guide member assembly 100 includes an outer flexible tubular assembly 102 and an inner stiffening member 104. The outer flexible tubular member 102 terminates in a threaded receptacle 106 at its proximal end and in a flange element 108 at its distal end. Conveniently, a metallic ring 110 is provided in order to provide a stop member for the inner stiffening member 104, as described in more detail hereinafter.

The nature of the outer flexible tubular member is not critical, and it may be in the form of a hollow polymeric tube, a metallic guidewire, or the like. The tubular member 102, however, should be sufficiently flexible so that it can be introduced through a relatively tortuous passage to a hollow body organ, as will be described with specific reference to retrograde access to the gall bladder hereinafter.

The inner stiffening member 104 terminates at a male thread element 112 at its proximal end, further having a knob attached to facilitate turning. A pin 116 having a rounded head projects from the distal end of the inner stiffening member 104, and the pin 116 and stiffening member 104 together define a shoulder 120, as best observed in FIG. 15. In this way, the inner stiffening member 104 may be inserted into lumen 122 of the flexible tubular member 102 until the shoulder 120 engages the stop ring 110. By then tightening down on the threaded member 112 within the housing 106, tension can be applied to the flexible guide member, causing a stiffening of the member along its entire length. Such a stiffened guide assembly 100 provides an excellent path for introducing a working catheter, dilator, or the like to hollow body organ. The stiffened guide member resists buckling, misalignment, and other deformation which might occur as the working catheter, dilator, or the like is introduced thereover. The stiffened member will additionally tend to straighten the tortuous path, improving access, and can further result in anchoring of the stiffened distal end, particularly when the stiffened end becomes lodged in restricted passages.

Figure 16:
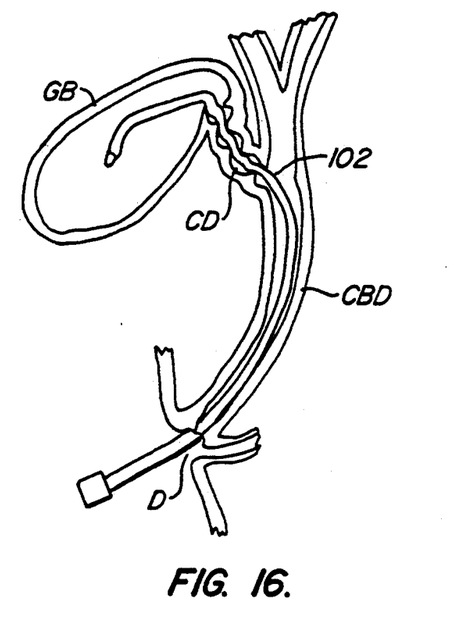
FIGS. 16-18 illustrate the use of the apparatus of FIGS. 13-15 in introducing a working catheter to the gall bladder in a retrograde manner.
Figure 17:
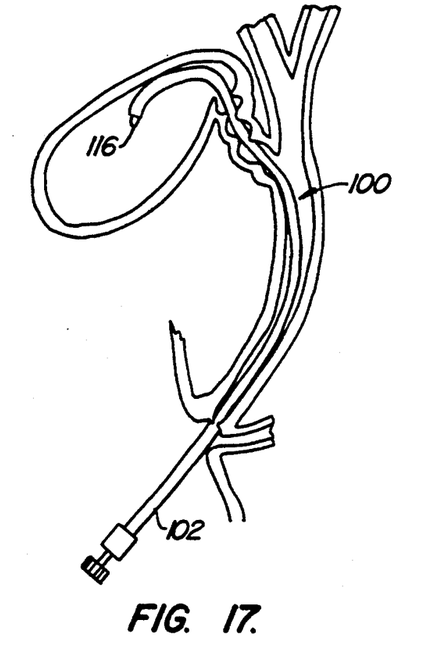
Figure 18:
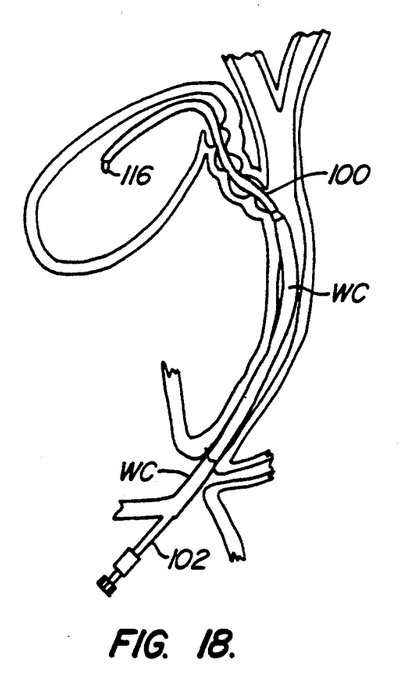

Referring now to FIGS. 16-18, the introduction of a working catheter to the gall bladder GB through the duodenum D, common bile duct CBD, and cystic duct CD, will be described. The outer flexible tube member 102 is first introduced through the path just described. The high flexibility of the outer flexible tube member 102, along with its small diameter relative to the working catheter WC, allows it to easily pass through the tortuous path which is encountered (FIG. 16). After the outer flexible tubular member 102 has been introduced, the inner stiffening member 104 will be inserted through the lumen 122, and tension will be applied in order to stiffen the resulting assembly 100. As can be seen in FIG. 17, sufficient tension will be applied to generally straighten the resulting assembly 100, particularly through the tortuous cystic duct.

Finally, referring to FIG. 18, a working catheter WC (or flexible slotted dilator) can be introduced over the exterior of the elongate guide member assembly 100 in a conventional manner. The tension provided by inner stiffening member 104 helps maintain the alignment of the guide member assembly 100 while the working catheter WC is being introduced, preventing withdrawal, buckling, kinking, and other deformation of the guide member as the catheter is advanced in the distal direction. Conveniently, the working catheter WC (or equivalent dilator) may include a slotted lumen (not illustrated) along all or part of its length to facilitate introducing the catheter over the guide member assembly 100. Alternatively, the working catheter WC (or dilator) may be pre-loaded on a proximal length of the guide member assembly 100 while the assembly is introduced and stiffened. The working catheter WC could then be moved forward after the distal end of the guide member assembly 100 is in place.

Although the foregoing invention has been described in detail for purposes of clarity of understanding, it will be obvious that certain modifications may be practiced within the scope of the appended claims.

What is claimed is:

1. An apparatus for forming a percutaneous penetration into a body cavity, said apparatus comprising:
   an elongate guide member having a proximal end, a distal end, means near the distal end for anchoring the guide member against a surface of the body cavity near the penetration, said anchoring means being selectively expandable to engage a region of the body cavity; and
   an elongate dilation member including a tapered distal tip and means for following the guide member into the body cavity, said following means being able to pass the expanded anchoring means when the dilation member is introduced over the guide member.

2. An apparatus as in claim 1, wherein the guide member is rigid.

3. An apparatus as in claim 1, wherein the guide member is flexible.

4. An apparatus as in claim 1, wherein the means for anchoring includes a deflectable element having a retracted position substantially within the elongate guide member and an radially projecting position, whereby the guide member may be percutaneously introduced with the deflectable element in its retracted position and anchored against the body cavity surface with the deflectable element in its radially projecting position.

5. An apparatus as in claim 4, wherein the deflectable element is a spring or is spring-mounted so that it assumes its radially projecting configuration when unconstrained, said apparatus further comprising means for constraining the deflectable element in its retracted position.

6. An apparatus as in claim 5, wherein the elongate guide member includes an axial lumen wherein the deflectable element is mounted and wherein the means for constraining the deflectable element comprises a stylet which is slidably received in the lumen and which engages the deflectable element to urge said element into its retracted position.

7. An apparatus as in claim 1, comprising at least two elongate dilation members having different sizes so that the dilation members may be successively introduced over the guide member to incrementally enlarge the percutaneous penetration.

8. An apparatus as in claim 4, wherein the means for following is an axial lumen having an axial slot for accommodating the deflectable element.

9. An apparatus comprising:
   a tubular guide member having a proximal end, a distal end, and an axial lumen therethrough;
   a stylet which is slidably received in the axial lumen of the guide member;
   a deflectable element near the distal end of the guide member, wherein said deflectable element assumes a retracted configuration when the stylet is in place and assumes a radially projecting configuration when the stylet is removed; and
   an elongate dilation member having means for passing over the guide member and clearing the deflectable element when said element is in its projecting configuration.

10. An apparatus as in claim 9, wherein the stylet is sharpened at one end and is sufficiently long so that said sharpened end will extend beyond the distal end of the cylindrical guide member when the stylet is in place within the central lumen, whereby the sharpened end of the stylet facilitates percutaneous penetration into a body cavity.

11. An apparatus as in claim 9, wherein the deflectable element is a spring-mounted finger that is retained in an axial orientation when the stylet is in place and assumes a radially projecting configuration when the stylet is removed.

12. An apparatus as in claim 11, wherein the tubular guide member has an axially elongate aperture near its distal end and the spring-mounted finger is disposed on the inner lumen wall opposite the aperture so that the finger will project radially outward through the aperture when the stylet is removed.

13. An apparatus as in claim 10, wherein the means for passing the elongate dilator over the guide member includes an axial lumen and slot which slidably receives the guide member while allowing clearance for the deflectable element in its laterally projecting configuration.

14. An apparatus as in claim 10, including at least one additional elongate dilation member having a larger cross-sectional area than the first dilator.

15. An apparatus comprising:
a tubular guide member having a proximal end, a distal end, and an axial lumen therethrough; and
an anchor wire slidably received in the lumen of the tubular guide member, said anchor wire having a spring tip which projects laterally from the guide member when the wire is moved to a preselected axial position within the guide member.

16. An apparatus as in claim 15, wherein the guide member has an aperture in its side wall, wherein the spring tip passes through the aperture where the anchor wire is in its preselected axial position.

17. An apparatus as in claim 16, wherein the spring tip is constrained within the guide member in a doubled-back configuration and is released by drawing the anchor wire proximally within the guide member.

18. An apparatus as in claim 15, wherein the distal end of the guide member terminates in a sharpened tip.

19. An apparatus as in claim 15, wherein the spring tip is constrained within the guide member in an elongated configuration and is released through a distal port on the guide member by extending the anchor wire in the distal direction, whereby the spring tip folds back upon the anchor wire to project laterally.

* * * * *